United States Patent [19]

Herd et al.

[11] 4,028,259

[45] June 7, 1977

[54] PROCESS FOR PREPARING A METAL SALT OF AN OXIDIZED, PHOSPHOSULFURIZED HYDROCARBON AND LUBRICANT COMPOSITIONS CONTAINING SAME

[75] Inventors: Richard S. Herd; Ferdinand P. Otto, both of Woodbury, N.J.

[73] Assignee: Mobil Oil Corporation, New York, N.Y.

[22] Filed: May 29, 1975

[21] Appl. No.: 582,027

[52] U.S. Cl. .............................. 252/46.7; 252/18; 252/32.7 R; 252/32.7 HC; 252/40.7; 252/42.1; 260/125; 260/139
[51] Int. Cl.² ........................................ C10M 1/48
[58] Field of Search ........ 252/18, 32.7 R, 32.7 HC, 252/40.7, 42.1, 46.7; 260/125, 139

[56] References Cited

UNITED STATES PATENTS

| | | | |
|---|---|---|---|
| 2,419,153 | 4/1947 | Musselman et al. | 252/32.7 R X |
| 2,779,737 | 1/1957 | Koft et al. | 252/18 X |
| 2,830,949 | 4/1958 | Berger et al. | 252/32.7 R X |
| 2,864,846 | 12/1958 | Gragson | 252/32.7 R X |
| 2,993,857 | 7/1961 | Sudholz | 252/32.7 R |
| 2,993,858 | 7/1961 | Sudholz | 252/32.7 R |

Primary Examiner—Delbert E. Gantz
Assistant Examiner—Andrew H. Metz
Attorney, Agent, or Firm—Charles A. Huggett; Raymond W. Barclay; Claude E. Setliff

[57] ABSTRACT

Phosphorus- and sulfur-containing metal salts are prepared by reacting a mixture comprising a metal oxide and a hydrocarbon in the presence of an oxidizing gas and then reacting this product with a phosphorus sulfide. The invention provides lubricant compositions containing the product.

5 Claims, No Drawings

PROCESS FOR PREPARING A METAL SALT OF AN OXIDIZED, PHOSPHOSULFURIZED HYDROCARBON AND LUBRICANT COMPOSITIONS CONTAINING SAME

BACKGROUND OF THE INVENTION

1. Field of the Invention

The invention relates to a process of preparing a metal salt and to lubricant compositions containing same. More particularly, it is related to a such metal salt made by reacting a hydrocarbon in the presence of a metal oxide, adding an oxidizing gas and then reacting the product thus obtained with a phosphorus sulfide and more metal oxide.

2. Discussion of the Prior Art

It is well known that hydrocarbon lubricating oils tend to oxidize in use in an engine with attendant formation of oxidation products which are acidic in character and which exert a corrosive action on the engine parts, such as the hard metal alloy bearings. Furthermore, it is well known that the gradual deterioration of the oil in use due to oxidation, etc. is attended by formation of carbonaceous sludge and lacquer which adheres to the engine parts, particularly the piston ring grooves and skirts, thereby lowering the efficiency of the engine and frequently causing the rings to stick. To counteract these conditions, the art has developed chemical agents which when added in small amounts to engine lubricating oils have the ability to greatly retard the oxidation of the oil in use. Agents have also been developed which have the ability to prevent deposition of sludge materials on the engine parts, thereby keeping the engine clean and free from the clogging and sticking effects normally encountered. These two types of chemical agents are known in the art as antioxidants and detergents, respectively. The present invention provides a new class of chemical products which exhibit both anti-oxidant and detergent properties. U.S. Pat. No. 2,830,949 discloses a class of compounds produced by reacting a hydrocarbon, which has been oxidized in the presence of a metal hydroxide, with a phosphorus sulfide and more metal hydroxide.

SUMMARY OF THE INVENTION

The present invention provides a method for the preparation of oil-soluble, phosphorus-, sulfur- and metal-containing reaction products which involves the steps of (1) forming a mixture of a hydrocarbon material, such as a petroleum oil, and a metal oxide, (2) contacting said mixture with an oxidizing gas at a temperature of from about 125° C. to about 325° C. to provide a metal-containing oxidized hydrocarbon product, (3) reacting the metal-containing oxidized hydrocarbon product with a phosphorus sulfide to provide a metal-, phosphorus- and sulfur-containing oxidized hydrocarbon product, (4) preparing a mixture of the product produced in step (3) with water and a metal oxide at a temperature below the boiling point of water, (5) substantially completely dehydrating the mixture formed in step (4) and (6) filtering the dehydrated mixture from step (5) to remove insolubles therefrom.

DISCUSSION OF SPECIFIC EMBODIMENTS

Due to the complex nature of the products provided by the invention, no exact chemical formula can be ascribed to them at this time and they are, therefore, best described by the process of producing them. However, analytical data indicate that these products are comprised principally of salts containing more equivalents of metal than so-called "normal salts". Thus, it has been found that products produced by the oxidation step of the present process contain about two equivalents of metal per equivalent of acid-hydrogen formed in the course of the oxidation. For example, when such an oxidation product, prepared by oxidizing a petroleum oil and containing 1.50% calcium, was de-metallized by means of strong hydrochloric acid, the resulting acidic product had a neutralization number (N.N.) of 21 and a saponification number of 18. This neutralization number would account for only 50% of the calcium, assuming the formation of normal salts. This indicated that the remaining 50% of the calcium is present in the product as some type of complexed or coordination compound.

When the products produced in the oxidation step are reacted with phosphorus sulfide and the resulting products reacted with additional metal oxide in accordance with the subsequent steps of the invention, the metal contents thereof are substantially increased. The manner in which this further amount of metal is incorporated into the ultimate products is not fully understood. However, without intending to limit the invention in any way by theoretical considerations, it would appear that the phosphorus sulfide reacts with oxygenated groups contained in the oxidized hydrocarbon molecules, such as aldehyde, ketone or alcohol groups, to form cross-link molecules. The phosphorus sulfide reaction with the oxidized hydrocarbon intermediate is often attended by substantial gel formation, particularly where the hydrocarbon reactant has been subjected to relatively strong oxidation. This gel, if formed, is broken by the addition of very small amounts of water.

The next step in the process involves the addition of water to hydrolyze the cross-linked molecules to form new acids which react with additional metal oxide to produce the ultimate salt products of the invention. As in the case of the oxidized oil intermediate products, de-metallization of the final product indicates that their metal contents are greater on an equivalent basis than the metal contents of normal salts.

It is important to note also that when reacting the oxidized product with phosphorus sulfide, gellation can be minimized or avoided completely by initially heating the reacting mixture to a temperature of from about 140° C to about 150° C, then immediately cooling it to a temperature of from about 115° C to about 125° C and maintaining it there for the remainder of the reaction period.

THE REACTANTS

The hydrocarbons utilizable as starting materials in the process of the invention may comprise any hydrocarbon or mixture of hydrocarbons capable of providing a product which is soluble in lubricating oil. In general, this solubility requirement is satisfied by hydrocarbons having molecular weights of from about 200 to about 1000, with those having molecular weights of from about 300 to about 600 being particularly suitable. The hydrocarbons may be saturated hydrocarbons and may be straight-chained, branch-chained or cyclic. Also, aromatic hydrocarbons which have substituent groups of sufficiently high molecular weight to provide an oil-solubilizing character to the final products can be used. Thus, alkaryl type hydrocarbons containing at least one aliphatic substituent of at least about 8 carbon atoms, or several such substituents totaling at least about 8 carbon atoms per molecule, are suitable. Examples of these would be octylbenzene, dodecylbenzene, waxbenzene and the like.

Petroleum oils and petroleum oil fractions, such as petrolatums, waxes, and the like, are a preferred class of hydrocarbon reactants, while refined oils, such as a solvent paraffinic neutral, are especially preferred. In terms of viscosity, oils having viscosities ranging from 2 to about 65 centistokes at 210° F may be used, with those having viscosities of from about 6 to about 45 centistokes at 210° F. being preferred. The characteristics of several different types of suitable oil stocks are shown in Table 1.

Table 1

| Oil | Gravity, ° API | Pour Point, ° F | K. V. at 210° F., cs | Avg. mol. wt. |
|---|---|---|---|---|
| Solvent-refined Mid-Continent distillate stock | 30.0 | 20 | 6.2 | 350 |
| Foots oil | 36.3 | 90 | 3.6 | 360 |
| Slack wax | 29.8 | 85 | 25.8 | 700 |
| Solvent-refined Mid-Continent bright stock | 25.8 | — | 25.9 | 720 |
| " | 26.3 | — | 32.9 | 840 |

The metal oxides utilizable as reagents in the invention are those of the metals of Groups I and II of Mendeleeff's Periodic Table of the Elements. Specifically, the oxides of calcium, sodium, potassium, barium, cobalt, strontium, zinc and magnesium are highly suitable, with calcium oxide being particularly preferred.

The phosphorus sulfide reactant used in the process may be either $P_2S_5$, $P_4S_7$ or $P_4S_3$, with $P_2S_5$ being preferred. Mixtures of the sulfides can also be used.

PROCESS CONDITIONS

In conducting the oxidation step of the process, the hydrocarbon reactant and the metal oxide reagent are charged to a reactor having means for the introduction of an oxidizing gas, such as air or oxygen. The amount of metal oxide charged to the hydrocarbon can range from about 1% up to about 10%, based on the weight of the hydrocarbon reactant. The reactants are mixed together and heated at a temperature of from about 100° C. to about 300° C., preferably 200° C. to 250° C., and maintained at this temperature while the oxidizing gas is passed through the mixture to effect oxidation of the hydrocarbon and reaction of the oxidized hydrocarbon with the metal oxide. The oxidation is continued until the hydrocarbon has attained a metal content of from about 0.2% to about 1.0% by weight.

It should be noted that the amount of metal oxide charged to the hydrocarbon prior to the oxidation reaction should, in all instances, be in excess of that eventually utilized in the oxidation. Thus, we have found that at least about 40 – 50% of the metal oxide charged should remain unreacted at the end of the oxidation. It has been found that the metal oxide when present in such amounts serves to prevent undesirable side reactions, such as oxidative polymerization, which are detrimental to the provision of products of the nature and quality herein contemplated, particularly from the standpoint of color and solubility in lubricating oil. Also, with respect to the weight of metal oxide charged per unit of weight of the hydrocarbon, although as much as 8% may be used (e.g. 8 grams of metal oxide per 100 grams of hydrocarbon), larger amounts provide no particular advantage.

The oxidation time required to incorporate the desired amount of metal into the hydrocarbon reactant will, of course, vary depending upon the conditions employed, such as the equipment used, the rate of oxygen or air introduction, the temperature, the amount of metal oxide charged, the type of hydrocarbon being oxidized and the like. As will be seen from the examples which follow, the oxidation times used varied from about 4 hours up to 6 hours. From a practical standpoint, it is, of course, desirable to use oxidation equipment and conditions which are conducive to effecting the oxidation to the desired extent in as short a time as possible. Accordingly, it is considered that modifications designed to increase the efficiency of the oxidation procedure, such as the use of oxidation catalysts and special reactors calculated to give a more efficient disbursal of the oxidizing gas in the hydrocarbon come within the broad purview of this invention.

Upon completion of the oxidation step the oxidized hydrocarbon product mixture may be filtered to remove the excess (unreacted) metal oxide, and the phosphorus sulfide reagent may then be added, or the phosphorus sulfide may be added directly to the oxidized hydrocarbon-metal oxide reaction mixture. In conducting the reaction, from about 6% to about 10% by weight (based on the weight of the hydrocarbon charge) of the phosphorus sulfide is mixed with the oxidized hydrocarbon product. The mixture is then heated to a temperature of from about 100° C to about 150° C for a sufficient time to complete the reaction. The reaction is usually complete in from about 30 minutes to about 2 hours. The temperature range is utilized as stated therein. That is, if the temperature reaches 150° C, immediate cooling is effected. The temperature may be varied within the aforesaid range without markedly affecting the final product.

The phosphorus contents of the finished products indicate that from about 85% to 95% of the phosphorus sulfide charged is reacted. However, the P/S ratio in the products ranges from about 0.5 to about 0.7 and for the most part averages about 0.6. This ratio is higher than 0.39 which is the P/S ratio in phosphorus pentasulfide, for example. It would appear, then, that some sulfur is lost in the reaction either as hydrogen sulfide, or it is removed as an oil-insoluble salt during the filtration step.

Gellation of the reaction mixture is apt to occur in the phosphorus sulfide reaction when the reaction temperature is kept at 150° C or higher. It does not, however, occur in the present invention, even if the temperature does reach 150° C. We emphasize that gellation is prevented if, when the temperature reaches 150° C, it is dropped to around 125° C and kept at this level for the remainder of the reaction.

In conducting the reaction of the phosphorus sulfide-oxidized hydrocarbon intermediate with the additional metal oxide in the presence of water, the metal oxide reagent can be either that which is already present in the reaction mixture (if the mixture was not filtered prior to the phosphorus sulfide reaction) or it can be a fresh charge of metal oxide. In any case, the amount of metal oxide present in the reaction mixture at this stage should be from about 2% to about 8% (based on the original hydrocarbon charge) the usual amount being about 4%. The amount of water necessary is small, generally from about 8% to about 12% being sufficient, although higher amounts may be used. The water is preferably added after cooling the reaction mixture to a temperature below its boiling point, preferably to about 90° C. Dehydration is then accomplished by heating the reaction mixture above the boiling point of water while passing a stream of nitrogen there through. The mixture is preferably heated to a temperature of from about 140° C to about 160° C and maintained at this temperature level until all of the water is driven off. The product is generally filtered at or near this latter temperature level in order to obtain relatively rapid filtration. Obviously, the dehydration may be accomplished in other ways, such as by adding a solvent (e.g. benzene), which may be subsequently distilled off as an azeotropic mixture.

The metal oxides used in the water-treating and dehydration steps of the invention are the same as those utilized in the oxidation step, i.e., the oxides of the metals of Groups I and II of the Periodic Table of the elements. However, mixed metal salt products, i.e. salt products containing more than one metal, can be produced in the invention by the use of one metal oxide in the oxidation step and a different metal oxide in the water-treating and dehydration steps.

A full understanding of the nature of the products of the invention and the manner of their preparation may be had by reference to the following examples. As the examples will show, the products made by the method of this invention, when compared to those made using calcium hydroxide (usually greasemaker's lime), require less oxidation time to achieve equivalent calcium levels, are lighter in color and are much easier to filter. It certainly was surprising that these three important advantages could be attained by the exchange of calcium oxide for the calcium hydroxide of the prior art. An additional unexpected advantage is less gellation due to controlled reaction temperatures in the phosphosulfurizing step.

The product prepared by the present process can be used to improve the oxidation and detergent properties of lubricants. The useful lubricants include (1) synthetic esters, such as one prepared from pentaerythritol and a mixed $C_5$–$C_9$ monocarboxylic acid, (2) mineral oils, both naphthenic and aromatic, (3) synthetic hydrocarbon lubricating oils, and (4) greases made from any of (1)–(3). The products may also be used as additives to cutting oils, in which water may be present (i.e. the oil may be oil-in-water or water-in-oil), hydraulic fluids, automatic transmission fluids and the like.

In the following Examples "ASTM Color" refers to the color test as set forth in ASTM D 1500.

EXAMPLE 1

Sixteen hundred grams of a solvent paraffinic neutral oil (30.9 API Gravity, a flash point of 475° F, a pour point of 15° F, a kinematic viscosity of 59.0 at 100° F and of 7.75 at 210° F) and having a number average molecular weight of 501, and 63.5 grams of Greasemakers' Lime (2.15 grams Ca/100 g oil charged) were charged into a 3 liter, 4 neck round bottom flask equipped with a glass stirrer with a glass "paddle type" blade, thermometer, Dean-Stark takeoff, water cooled reflux condenser and a glass frit for sparging air into the mixture. The mixture was air blown for 11 hours at 210° C using an air rate of 5.1 cubic feet per hour. The product contained, by analysis: 0.81% Ca. ASTM Color (2% wt in xylenes) = D 4.0.

This Example illustrates the long oxidation time required to reach 0.8% Ca in oil and the dark color of the product.

EXAMPLE 2

Sixteen hundred grams of a solvent paraffinic neutral oil (same as used in Example 1) and 48 grams of pulverized calcium oxide (2.15 grams Ca/100 g oil charged) were utilized. The conditions were the same as for Example 1, except the oxidation time was 5.2 hours. Product contains, by analysis: 0.80% Ca. ASTM Color (2% wt in xylenes) = D 0.5.

This example illustrates the short oxidation time required to reach 0.8% Ca in oil and the light color of the product.

EXAMPLE 3

One hundred fifty grams of the product of Example 1, (unfiltered), 12 grams of $P_2S_5$ and 75g of diluent oil were charged into a 500 ml, 4 neck flask equipped with a thermometer, Dean-Stark takeoff, water cooled condenser and a magnetic spin bar for stirring. The mixture was heated to 150° C and then immediately cooled to 125° C over a period of about 10 minutes and held at 125° C for 1.8 hours. (The total reaction time after reaching 150° C was 2 hours). The mixture was then cooled to 90° C and 15 grams of water was added slowly. The mixture was then cooled to 75° C and sparged with nitrogen for 1 hour at a rate of 320 cc/minute. After sparging, 75 grams of diluent oil and 8 grams of Greasemaker's Lime (4.3 g of Ca) were added, heated to 90° C and held for one hour at this temperature. Water was removed by distillation. When the temperature reached 100° C, a slight nitrogen sparge was started. At 110° C the pressure was reduced to 23 inches mercury. At 145° C, the pressure was reduced to 28 inches of pressure and the mixture held for 0.5 hours at these conditions.

One hundred grams of unfiltered product was filtered at 140° C through a No. 0 Buckner funnel using 1 gram of Hyflo precoat on a No. 2 Whatman filter paper and 2.5 grams of Hyflo as filter-aid. Approximately 23 inches of mercury was used. The filtration rate was very slow, with only 50.5 grams recovered in 20 min.

Analysis:
2.03% Ca
1.0% P
1.52% S
ASTM Color (2% wt in xylenes) = 4.5

This Example illustrates the poor filtration and dark color obtained when using Greasemaker's Lime (Ca(OH)$_2$).

EXAMPLE 4

The procedure in this Example was the same as used in Example 3, except that 155 grams of unfiltered Example 2 product and 6 grams of calcium oxide (4.3 g Ca) were used for the neutralization step.

Filtration conditions were the same as those set forth in Example 3. The filtration rate was fast, and 96.4 grams of product were recovered in 8 minutes.

Analysis:
1.86% Ca
0.95% P
1.45% S
ASTM Color (2% wt in xylenes) = D 2.5

This Example illustrates the fast filtration rate and light color obtained when using calcium oxide (pulverized).

SUMMARY OF DATA

Table 1
CALCIUM OXIDIZED OIL

| Example | Calcium Source | Oxidation Time, Hrs. | % Ca | Color[1] |
|---------|----------------|----------------------|------|----------|
| 1 | Ca(OH)$_2$ | 11 | 0.81 | D 4.0 |
| 2 | CaO | 4.1 | 0.80 | D 0.5 |

Table 2
CALCIUM OXIDIZED OIL - P$_2$S$_5$ PRODUCTS

| Example | Calcium Source | % Ca | % P | % S | Color[1] | Filtration Rate |
|---------|----------------|------|-----|-----|----------|-----------------|
| 3 | Ca(OH)$_2$ | 2.03 | 1.0 | 1.52 | 4.5 | slow |
| 4 | CaO | 1.86 | 0.95 | 1.45 | D 2.5 | fast |

[1] 2% wt in xylenes

EVALUATION OF PRODUCTS

The additive of Example 4 was tested as an antioxidant in a furfuryl extracted 150 sec. paraffinic neutral oil. The test was carried out by passing air through a sample of the oil at 5 liters per hour for 40 hours at a temperature of 325° F. Present in the oil were samples of metals capable of acting as oxidation accelerators, namely, iron, copper, lead and aluminum. The lead sample was weighted before and after each test to determine the loss of weight, lead being presumed the most susceptible to loss in this test. The capability of an antioxidant is measured, among other things, by the increase in the kinematic viscosity at 210° F. The results are tabulated in the following table:

| Medium | % Viscosity Increase ($\Delta$ KV at 210° F) |
|--------|-----------------------------------------------|
| Base Oil | 202 |
| Base Oil + 1% Ex. 4 | 174 |
| Base Oil + 2% Ex. 4 | 161 |

We claim:

1. A process for preparing an oil-soluble, phosphorus and sulfur containing oxidized oil reaction product which comprises the steps of (1) preparing a mixture comprising (a) a hydrocarbon having a molecular weight of from about 200 to about 1000 and (b) from about 1% to about 10% based on the weight of said hydrocarbon of a metal oxide, the metal being selected from Group 1 or Group 2 of the Periodic Table, (2) contacting said mixture with an oxidizing gas at from about 100° C to about 300° C to effect oxidation of said hydrocarbon and reaction of said metal oxide with the oxidized hydrocarbon, (3) continuing the oxidation for a time sufficient to incorporate from about 0.2% to about 1.0% by weight of metal into the oxidized hydrocarbon, (4) reacting, at from about 100° C to about 150° C, the product from step (3) with a phosphorus sulfide to form a phosphorus-, sulfur- and metal-containing product, the amount of phosphorus sulfide used being from about 6% to about 10% by weight of the oxidized hydrocarbon charge, (5) reacting the reaction product of step (4) with additional metal oxide in the presence of water, the amount of metal oxide present at this stage being from about 2% to about 8% of the original hydrocarbon charge and (6) substantially completely dehydrating the mixture formed in step (5).

2. The process of claim 1 in which the phosphorus sulfide is phosphorus pentasulfide.

3. The process of claim 1 in which the hydrocarbon is a solvent refined paraffinic neutral oil having a number average molecular weight of about 500.

4. The process of claim 1 wherein in step (4) the temperature of reaction is initially carried to about 140° to about 150° C, then immediately reduced to about 115° to about 125° C for the remainder of the reaction time.

5. The process of claim 1 in which the metal oxide is calcium oxide.

* * * * *